(12) United States Patent
Kerschner et al.

(10) Patent No.: US 8,017,687 B2
(45) Date of Patent: Sep. 13, 2011

(54) SWOLLEN SILICONE COMPOSITION AND PROCESS OF PRODUCING SAME

(75) Inventors: Judith Kerschner, Hawthorne, NJ (US); Gerald J. Murphy, Poughkeepsie, NY (US); John Nicholson, Ramsey, NJ (US)

(73) Assignee: Momentive Performance Materials Inc., Albany, NY (US)

(*) Notice: Subject to any disclaimer, the term of this patent is extended or adjusted under 35 U.S.C. 154(b) by 1412 days.

(21) Appl. No.: 11/274,450

(22) Filed: Nov. 15, 2005

(65) Prior Publication Data

US 2007/0112112 A1    May 17, 2007

(51) Int. Cl.
C08G 77/06 (2006.01)
(52) U.S. Cl. ...................................... 524/731; 424/401
(58) Field of Classification Search .................. 524/731; 424/401
See application file for complete search history.

(56) References Cited

U.S. PATENT DOCUMENTS

| | | | |
|---|---|---|---|
| 2,970,150 A * | 1/1961 | Bailey .......................... | 549/215 |
| 3,455,839 A | 7/1969 | Rauner | |
| 3,984,347 A | 10/1976 | Keil | |
| 4,145,308 A | 3/1979 | Simoneau et al. | |
| 4,188,451 A | 2/1980 | Humphrey, Jr. | |
| 4,197,335 A | 4/1980 | Goossens | |
| 4,198,465 A | 4/1980 | Moore et al. | |
| 4,235,954 A | 11/1980 | Humphrey, Jr. | |
| 4,242,381 A | 12/1980 | Goossens et al. | |
| 4,243,720 A | 1/1981 | Schroeter et al. | |
| 4,284,685 A | 8/1981 | Olson et al. | |
| 4,298,632 A | 11/1981 | Schroeter et al. | |
| 4,308,317 A | 12/1981 | Olson et al. | |
| 4,395,352 A | 7/1983 | Kulkarni et al. | |
| 4,427,801 A | 1/1984 | Sweet | |
| 4,478,876 A | 10/1984 | Chung | |
| 4,584,355 A | 4/1986 | Blizzard et al. | |
| 4,585,830 A | 4/1986 | Sweet | |
| 4,639,489 A | 1/1987 | Aizawa et al. | |
| 4,749,740 A | 6/1988 | Aizawa et al. | |
| 4,814,418 A | 3/1989 | Miyake et al. | |
| 4,842,941 A | 6/1989 | Devins et al. | |
| 4,863,802 A | 9/1989 | Moore et al. | |
| 4,902,578 A | 2/1990 | Kerr, III | |
| 4,929,506 A | 5/1990 | Kerr, III et al. | |
| 4,978,471 A | 12/1990 | Starch | |
| 4,983,316 A | 1/1991 | Starch | |
| 4,987,169 A | 1/1991 | Kuwata et al. | |
| 5,236,986 A | 8/1993 | Sakuta | |
| 5,252,250 A | 10/1993 | Endo et al. | |
| 5,283,004 A | 2/1994 | Miura | |
| 5,380,464 A | 1/1995 | McGee et al. | |
| 5,412,004 A * | 5/1995 | Tachibana et al. .............. | 524/27 |
| 5,514,828 A | 5/1996 | Evans | |
| 5,654,352 A | 8/1997 | MacDonald | |
| 5,654,362 A | 8/1997 | Schulz, Jr. et al. | |
| 5,693,256 A | 12/1997 | Sawicki et al. | |
| 5,760,116 A | 6/1998 | Kilgour et al. | |
| 5,773,407 A | 6/1998 | Lai et al. | |
| 5,811,487 A | 9/1998 | Schulz, Jr. et al. | |
| 5,834,578 A | 11/1998 | Evans et al. | |
| 5,861,453 A | 1/1999 | Datz-Siegel et al. | |
| 5,880,210 A | 3/1999 | Schulz, Jr. et al. | |
| 5,900,190 A | 5/1999 | Evans et al. | |
| 5,914,362 A | 6/1999 | Brecht et al. | |
| 6,060,546 A | 5/2000 | Powell | |
| 6,083,900 A | 7/2000 | Auguste et al. | |
| 6,207,722 B1 | 3/2001 | Juen et al. | |
| 6,207,782 B1 | 3/2001 | Czech et al. | |
| 6,271,295 B1 | 8/2001 | Powell | |
| 6,331,604 B1 | 12/2001 | Wang et al. | |
| 6,444,745 B1 | 9/2002 | Kilgour et al. | |
| 6,521,587 B1 | 2/2003 | L'Hostis et al. | |
| 6,531,540 B1 | 3/2003 | O'Brien | |
| 6,538,061 B2 | 3/2003 | Chaiyawat et al. | |
| 6,605,183 B1 | 8/2003 | Rautschek et al. | |
| 6,759,479 B2 | 7/2004 | O'Brien | |
| 6,994,846 B2 | 2/2006 | L'Alloret | |
| 7,064,173 B2 | 6/2006 | Rubinsztajn et al. | |
| 7,241,851 B2 | 7/2007 | Cella et al. | |
| 2003/0118530 A1 | 6/2003 | O'Brien et al. | |
| 2003/0235548 A1 | 12/2003 | Lu | |
| 2004/0127668 A1 | 7/2004 | Rubinsztajn et al. | |
| 2004/0197284 A1 | 10/2004 | Auguste | |
| 2004/0202812 A1 | 10/2004 | Congard | |
| 2004/0228821 A1 | 11/2004 | Sunkel et al. | |
| 2005/0008598 A1 | 1/2005 | Lu et al. | |
| 2005/0008599 A1 | 1/2005 | Lu et al. | |
| 2005/0033001 A1 | 2/2005 | Cella et al. | |
| 2005/0048016 A1 | 3/2005 | Lebreton | |
| 2005/0065226 A1 | 3/2005 | Mirone | |
| 2005/0069564 A1 | 3/2005 | Eversheim | |
| 2005/0265942 A1 | 12/2005 | Rajaraman | |
| 2005/0267258 A1 | 12/2005 | Rajaraman | |
| 2006/0115657 A1 | 6/2006 | Griswold | |

FOREIGN PATENT DOCUMENTS

EP    0802228 A2    10/1997

(Continued)

OTHER PUBLICATIONS

Grant Industries Gransil AM-8 Gel Specification Sheets © 1994; http://www.grantinc.com/Personal_Care/SpecShts/Med_Volatile/Med_Volatile%20Gels.htm , 2 pages.
Grant Industries Gransil AM-8 Gel Specification Sheets © 1994; http://www.grantinc.com/Personal_Care/SpecShts/med_volatile/GRANSIL_AM-8Gel.htm, 2 pages.
U.S. Appl. No. 11/274,832, filed Nov. 15, 2005, Proctor et al.
U.S. Appl. No. 11/474,571, filed Jun. 2006, Falk et al.

(Continued)

*Primary Examiner* — Margaret Moore
(74) *Attorney, Agent, or Firm* — Dominick G. Vicari

(57) ABSTRACT

There is provided herein, in one specific embodiment, silicone composition(s) comprising unique combination(s) of silicone polymer and alkyltrisiloxane(s) which can produce silicone composition(s) with lower solids content than silicone compositions that use other than alkyltrisiloxane(s); while still maintaining a desirable viscosity.

29 Claims, No Drawings

FOREIGN PATENT DOCUMENTS

| | | |
|---|---|---|
| EP | 0802231 A2 | 10/1997 |
| EP | 0905198 B1 | 9/1998 |
| EP | 0934959 A1 | 8/1999 |
| EP | 1002825 A2 | 5/2000 |
| EP | 1016442 A2 | 7/2000 |
| EP | 1075863 A2 | 2/2001 |
| EP | 1082953 | 3/2001 |
| EP | 1391193 | 2/2004 |
| EP | 1481660 | 12/2004 |
| GB | 1110207 | 1/1967 |
| GB | 2103230 | 2/1983 |
| JP | 63152634 | 6/1988 |
| JP | 1306428 | 12/1989 |
| JP | 2142896 | 5/1990 |
| JP | 4211499 | 8/1992 |
| JP | 05261207 A | 10/1993 |
| JP | 8337655 | 12/1996 |
| JP | 2000-143989 | 1/2000 |
| JP | 2005 314358 A | 11/2005 |
| JP | 2005314358 | 11/2005 |
| WO | WO98/18849 | 5/1998 |
| WO | WO 2004/103323 | 12/2004 |
| WO | WO 2005/118682 | 12/2005 |

* cited by examiner

SWOLLEN SILICONE COMPOSITION AND PROCESS OF PRODUCING SAME

BACKGROUND OF THE INVENTION (1) Field of the Invention

The invention relates to composition of swollen silicone polymer, process for making the same and personal care formulations using the same.

(2) Description of Related Art

The personal care industry thrives on being able to deliver multiple performance products based on mixtures of several components, with each component having a performance and compatibility profile, which can lend that component to properties that are important to or desirable in certain final product formulations. One desirable property is the ability to provide a silky initial feel. This property can be derived from the use of cyclic siloxanes in the formulation. In addition to the silky initial feel, cyclic siloxanes used in silicone gels can simultaneously maintain a high viscosity product, which can also be desirable for various product formulations. Although cyclic siloxanes provide the desired feel characteristics, they are low viscosity, highly flowable liquids. Thus, they are not easily held in a formulation, preferring rather to separate and flow out of a given container or flow uncontrollably across the skin when used in a specific application. Further desirable properties include achieving an initial silky feel while providing a smooth, low-residue feel upon dry-down, as well as achieving a high transfer resistance in as short a period as possible.

Cyclic siloxanes have limitations in terms of their performance and compatibility profile. A desired performance and/or compatibility profile possessing the various desirable properties described above is not always achievable by using a cyclic siloxane. Certain applications can require a different performance and/or compatibility profile that cannot be met by the use of cyclic siloxanes.

In addition to providing a particular performance and/or compatibility profile, cyclic siloxanes provide effective swelling of silicone polymer. In addition to cyclic siloxanes, linear siloxane fluids have been used to swell silicone polymer and to provide a different performance and/or compatibility profile and different end application benefits from that of cyclic siloxanes. These linear siloxane fluids are made via an equilibrium process and comprise a distribution of molecular weights. Unfortunately, up to now, the use of linear siloxanes has required a much higher level of silicone polymer (solids) to obtain the desired viscosities that are obtainable through cyclic siloxanes. Using higher amounts of solids has processing and cost disadvantages. In addition, using higher amounts of solids can cause "balling" of a product on the skin, which is a negative sensory attribute.

BRIEF DESCRIPTION OF THE INVENTION

In this brief description it is noted that the present inventors have unexpectedly discovered, in one specific embodiment, swollen cross-linked silicone polymer network composition(s). This swollen cross-linked silicone polymer network composition comprises a unique combination(s) of silicone polymer network and linear organosiloxane, which can produce swollen cross-linked silicone polymer network with desirable viscosity and solids content.

Thus in one embodiment, there is provided a first swollen cross-linked silicone polymer network composition comprising:

a) the reaction product of

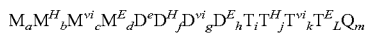

where $M = R^1 R^2 R^3 SiO_{1/2}$;

$M^H = R^4 R^5 HSiO_{1/2}$;

$M^{vi} = R^6 R^7 R^8 SiO_{1/2}$;

$M^E = R^9 R^{10} R^E SiO_{1/2}$;

$D = R^{11} R^{12} SiO_{2/2}$;

$D^H H = R^{13} HSiO_{2/2}$;

$D^{Vi} = R^{14} R^{15} SiO_{2/2}$;

$D^E = R^{16} R^E SiO_{2/2}$ $T = R^{17} SiO_{3/2}$ $T^H = HSiO_{3/2}$;

$T^{vi} = R^{18} SiO_{3/2}$;

$T^E = R^E SiO_{3/2}$; and $Q = SiO_{4/2}$ where $R^1$, $R^2$, $R^3$, $R^{11}$, $R^{12}$ and $R^{17}$ are independently monovalent hydrocarbon radicals having from one to sixty carbon atoms; $R^4$, $R^5$ and $R^{13}$ are independently monovalent hydrocarbon radicals having from one to sixty carbon atoms or hydrogen; $R^6$ is a monovalent unsaturated hydrocarbon radical having from two to ten carbon atoms, and $R^7$ and $R^8$ are independently monovalent hydrocarbon radicals having from one to sixty carbon atoms; $R^{14}$ is a monovalent unsaturated hydrocarbon radical having from two to ten carbon atoms; and $R^{15}$ is a monovalent hydrocarbon radical having from one to sixty carbon atoms; $R^{18}$ is a monovalent unsaturated hydrocarbon radical having from two to ten carbon atoms; $R^9$, $R^{10}$ and $R^{16}$ are independently monovalent hydrocarbon radicals having from one to sixty carbon atoms or $R^E$; each $R^E$ is independently a monovalent hydrocarbon radical containing one or more oxirane moieties having from one to sixty carbon atoms; the stoichiometric subscripts a, b, c, d, e, f, g, h, i, j, k, L, and m, are either zero or positive subject to the following limitations: $a+b+c+d \geq 1$; $d+h+L \geq 1$ and $b+f+j \geq 1$; and, b) a swelling amount of an alkyltrisiloxane wherein said reaction product is swollen by said alkyltrisiloxane to form first silicone composition and wherein said first silicone composition possesses a lower solids content than a solids content present in a second silicone composition comprising said reaction product and a linear silicone fluid other than an alkyltrisiloxane, whereby second silicone composition and first silicone composition have equivalent viscosities.

In another embodiment there is also provided a process of producing said first silicone composition comprising combining said reaction product (a) and said swelling amount of an alkyltrisiloxane (b).

DETAILED DESCRIPTION OF THE INVENTION

Applicants have discovered, in one embodiment, that first swollen cross-linked silicone polymer network composition (first silicone composition) with low solids content can be obtained by using alkyltrisiloxane to swell reaction product (a).

As used herein the term trisiloxane is used both specifically as a trisiloxane also collectively includes generically higher molecular weight well defined linear siloxanes having a higher number of D repeat units such as tetrasiloxanes pentasiloxanes and the like or alternatively low molecular weight well defined linear siloxanes such as disiloxanes; such higher order or lower order linear siloxanes are subtended by the cumulative usage herein defined as long as the phenomenological properties and parameters or solid content at constant viscosity are met.

As used herein the terms polyorganosiloxane and organopolysiloxane are interchangeable one with the other.

It will be understood herein that all uses of the term centistokes were measured at 25 degrees celsius.

It will be understood herein that all specific, more specific and most specific ranges recited herein comprise all subranges therebetween.

It will be understood herein that all percent ranges are weight percent based upon total weight of first silicone composition unless stated otherwise.

As used herein, the terminology "reaction product (a)" means a three dimensionally extending structure comprising interconnected polysiloxane chains. In one specific embodiment, reaction product (a) contains at least one fluid component within interstices of reaction product (a) that is present as a result of generating cross-linked reaction product (a). The term "interstices" is used herein in reference to a reaction product (a) to denote spaces within reaction product (a), that is, spaces between the polysiloxane chains of the reaction product (a).

In one specific embodiment, reaction product (a) is cross-linked silicone polymer network that is insoluble in said fluid component, but that is capable of being swollen by said fluid component. The amount of crosslinking present in the reaction product (a) can be characterized with respect to the degree of swelling exhibited by reaction product (a) in the fluid component. In one specific embodiment, the cross-linked structure of the reaction product (a) is effective to allow reaction product (a) to be swollen by a low molecular weight silicone fluid, from its original volume to a swollen volume that is a factor of specifically from about 1.01 to about 5000, more specifically, of from about 2 to about 1000, and most specifically of from about 5 to about 500, times its original volume. In another specific embodiment, the original volume of reaction product (a) can be determined, for example, by extracting or evaporating all fluid component present in the first silicone composition described herein, to leave the original volume, that is, the volume of the reaction product (a) in the absence of fluid component.

In another specific embodiment, reaction product (a) is a swollen cross-linked silicone polymer network gel, more specifically a swollen cross-linked silicone polymer network gel that can be swollen to a volume as described above. It will be understood herein that any and all gels described herein are formed following the polymerization of an epoxy-functional organosiloxane to form a polyether siloxane copolymer network, which is known to those skilled in the art and is described in U.S. Pat. No. 6,531,540, the contents of which are incorporated herein by reference in their entirety.

In one embodiment solids can generally be defined as any particles that are swollen by fluid component in first silicone composition described herein. In one embodiment, particles that are swollen by fluid component in first silicone composition are particles of reaction product (a) as described herein. In another embodiment, as stated above, certain applications require first silicone composition with a lower level of solids than second silicone composition, while still maintaining a desired viscosity. In one embodiment herein, solids content is measured by evaporation or extraction of all of the fluid component from first silicone composition and reported as weight percent of the total weight of first silicone composition. In one specific embodiment, solids content can be a lower solids content than that of second silicone composition comprising reaction product (a) and a linear silicone fluid other than alkyltrisiloxane. In one specific embodiment, solids level can be measured by evaporation of the fluid component by heating in an oven at 150° C.

A desired viscosity as used herein can vary greatly depending upon application of first silicone composition described herein. In one specific embodiment, first silicone composition can be used in personal care formulations as described herein. A personal care formulation can also have any viscosity that would be desirable for the particular personal care formulation.

As used herein, cross-link density is used to define the extent of the cross-linking between polysiloxane chains. Thus, "low" cross-link density would be used to describe a loosely cross-linked network having more interstitialspace between the polyorganosiloxane chains, whereas "high" cross-link density would be used to describe a more tightly cross-linked structure with smaller orfewer, interstitialspaces between the polyorganosiloxane chains. As used herein, cross-link structure means a three dimensionally extending structure comprising interconnected polyethersiloxane copolymer chains. At high cross-link densities in a cross-linked polymer the polymer will not swell significantly in the presence of a compatible solvent and thus will not imbibe much solvent.

In one specific embodiment herein, first silicone composition can have a lower solids content than that of second silicone composition comprising other than alkyltrisiloxane such as the non-limiting example of cyclic siloxane.

In one more specific embodiment, a lower solids content can entail, where first silicone composition has a given cross-linked structure and a given cross-link density and said lower solids content of first silicone composition is at least about 10 percent lower than the solids content for second silicone composition which has an equivalent cross-linked structure and an equivalent cross-link density to first silicone composition; and where first silicone composition has a viscosity of greater than about 100,000 centistokes.

In one more specific embodiment, a lower solids content can entail, where first silicone composition has a given cross-linked structure and a given cross-link density and said lower solids content of first silicone composition is at least about 25 percent lower than the solids content for second silicone composition which has an equivalent cross-linked structure and an equivalent cross-link density to first silicone composition; and where first silicone composition has a viscosity of greater than about 150,000 centistokes.

In one more specific embodiment, a lower solids content can entail, where first silicone composition has a given cross-linked structure and a given cross-link density and said lower solids content of first silicone composition is at least about 40 percent lower than the solids content for second silicone composition which has an equivalent cross-linked structure and an equivalent cross-link density to first silicone composition; and where first silicone composition has a viscosity of greater than about 200,000 centistokes.

In one other embodiment, any of the above described viscosities for swollen cross-linked silicone polymer network composition can be obtained at any of the above described ranges of solids content.

In one specific embodiment, reaction product (a) can be any known or commercially used reaction product (a) provided that reaction product (a) can be swollen to a swollen volume as described above. In another specific embodiment, reaction product (a) is an organopolysiloxane. In yet a further specific embodiment, reaction product (a) can be a three-dimensional organo-functional polyorganosiloxane which contains polyether cross-links. In yet still a further specific embodiment, said three-dimensional organo-functional polyorganosiloxane which contains polyether cross-links can be formed as a result of the polymerization of an epoxy-functional organosiloxane.

In yet another more specific embodiment, the organo group(s) of organopolysiloxane can be any organo group commonly associated with such polymers and can generally be selected from the non-limiting examples of alkyl radicals of 1 to about 60 carbon atoms, such as methyl, ethyl, propyl; cycloalkyl radicals such as cyclohexyl, cycloheptyl, cyclooctyl; mononuclear aryl radicals such as phenyl, methylphenyl, ethylphenyl; alkenyl radicals such as vinyl and allyl; alkylene oxide radicals, such as ethylene oxide, propylene oxide and mixtures thereof; and haloalkylradicals such as 3,3,3,trifluoropropyl. In a more specific embodiment, the organo groups are alkyl radicals of 1 to 8 carbon atoms, and are most specifically methyl. In one embodiment, polyorganosiloxane has some hydroxyl groups in the polymer. In one specific embodiment the organo group(s) of organopolysiloxane can be any of the organic functional groups described in U.S. Pat. No. 6,531,540 the contents of which are incorporated herein by reference. It will be understood that the nomenclature used in U.S. Pat. No. 6,531,540 regarding hydrocarbon radicals will deemed to be equivalent to organo groups as they are described herein, in that any hydrocarbon radical described in U.S. Pat. No. 6,531,540 can be used as an organo group as is described herein so that the terms hydrocarbon radical as it is described in U.S. Pat. No. 6,531,540 and organo group(s) as used herein is interchangeable. In one embodiment herein it will be understood that any organo groups described herein can be present on said organopolysiloxane or can be bonded to said organopolysiloxane through a reaction with an organic compound, such as the non-limiting example of an alpha-olefin.

In one specific embodiment herein, reaction product (a) can have the general formula:

$$M_a M^H_b M^{vi}_c M^E_d D_e D^H_f D^{vi}_g D^E_h T_i T^H_j T^{vi}_k T^E_L Q_m$$

where $$M = R^1 R^2 R^3 SiO_{1/2};$$

$$M^H = R^4 R^5 HSiO_{1/2};$$

$$M^{vi} = R^6 R^7 R^8 SiO_{1/2};$$

$$M^E = R^9 R^{10} R^E SiO_{1/2};$$

$$D = R^{11} R^{12} SiO_{2/2};$$

$$D^H = R^{13} HSiO_{2/2};$$

$$D^{vi} = R^{14} R^{15} SiO_{2/2};$$

$$D^E = R^{16} R^E SiO_{2/2}$$

$$T = R^{17} SiO_{3/2}$$

$$T^H = HSiO_{3/2};$$

$$T^{vi} = R^{18} SiO_{3/2};$$

$$T^E = R^E SiO_{3/2};$$ and $$Q = SiO_{4/2}$$

where $R^1$, $R^2$, $R^3$, $R^{11}$, $R^{12}$ and $R^{17}$ are independently monovalent hydrocarbon radicals having from one to sixty carbon atoms; $R^4$, $R^5$ and $R^{13}$ are independently monovalent hydrocarbon radicals having from one to sixty carbon atoms or hydrogen; $R^6$ is a monovalent unsaturated hydrocarbon radical having from two to ten carbon atoms, and $R^7$ and $R^8$ are independently monovalent hydrocarbon radicals having from one to sixty carbon atoms; $R^{14}$ is a monovalent unsaturated hydrocarbon radical having from two to ten carbon atoms; and $R^{15}$ is a monovalent hydrocarbon radical having from one to sixty carbon atoms; $R^{18}$ is a monovalent unsaturated hydrocarbon radical having from two to ten carbon atoms; $R^9$, $R^{10}$ and $R^{16}$ are independently monovalent hydrocarbon radicals having from one to sixty carbon atoms or $R^E$; each $R^E$ is independently a monovalent hydrocarbon radical containing one or more oxirane moieties having from one to sixty carbon atoms; the stoichiometric subscripts a, b, c, d, e, f, g, h, i, j, k, L, and m, are either zero or positive subject to the following limitations: $a+b+c+d \geq 1$; $d+h+L \geq 1$ and $b+f+j \geq 1$.

In another embodiment there is also provided a process of producing said first silicone composition comprising combining said reaction product (a) and said swelling amount of an alkyltrisiloxane (b).

In yet a further specific embodiment, reaction product (a) having the formula $M_a M^H_b M^{vi}_c M^E_d D_e D^H_f D^{vi}_g D^E_h T_i T^H_j T^{vi}_k T^E_L Q_m$ as described above, can comprise the reaction product of (I) a composition comprising the formula:

$$M^H_n D_o D^H_p M^H_{2-n}$$

where $$M^H = R^{19} R^{20} HSiO_{1/2};$$

$$D = R^{21} R^{22} SiO_{2/2};$$ and, $$D^H = R^{23} HSiO_{2/2}$$

where $R^{19}$, $R^{20}$, and $R^{23}$ are independently monovalent hydrocarbon radicals having from one to sixty carbon atoms or hydrogen; $R^{21}$ and $R^{22}$ are independently monovalent hydrocarbon radicals having from one to sixty carbon atoms; the stoichiometric subscripts n, o, and p are zero or positive subject to the limitations: o is a number greater than 10, p is a number from zero to about 20, n is a number from zero to two, subject to the limitation that n+p is from 1 to about 20; (II) alkenyl cycloalkylene oxide such as the non-limiting example of vinyl cyclohexene oxide; (III) alpha-olefin fraction such as Alpha Olefin Gulftene C30+ available from Chevron or $C_{16-18}$ alpha olefin obtained from Innovene; (IV) linear siloxane and optionally cyclic siloxane, where linear siloxane can comprise the non-limiting example of alkyltrisiloxane, specifically ethyltrisiloxane (ETS) such as the non-limiting example of heptamethylethyltrisiloxane, octyltrisiloxane (OTS), such as the non-limiting example of heptamethyloctyltrisiloxane, hexyltrisiloxane such as the non-limiting example of heptamethylhexyltrisiloxane and any other alkyltrisiloxanes described herein (V) catalyst such as the non-limiting example of platinum catalyst, more specifically Karstedt's Catalyst; (VI) epoxide polymerization catalyst formed through the interaction of platinum with a Si—H bond containing compound such as the non-limiting example of $MD^H_{50}M$ in fluid component such as the non-limiting examples of ethyltrisiloxane and optionally decamethyl cylcopentasiloxane; and (VII) agent for quenching residual Si—H functionality such as the non-limiting example of $C_{16-18}$ alpha olefin.

In one other specific embodiment herein reaction product (a) having the formula $M_a M^H{}_b M^{vi}{}_c M^E{}_d D_e D^H{}_f D^{vi}{}_g D^E{}_h T_i T^H{}_j T^{vi}{}_k T^E{}_L Q_m$ as described above, can further comprise the reaction product of (I) a composition having the formula $M^H D_{133} D^H{}_{2.5} M^H$; (II) vinyl cyclohexene oxide; (III) alpha olefin Gulftene C30+ available from Chevron; (IV) ETS and optionally decamethylcyclopentasiloxane; (V) solution of a platinum catalyst (Karstedt's Catalyst); (VI) $MD^H{}_{50}M$ in ETS and optionally decamethyl cylcopentasiloxane; and (VII) $C_{16-18}$ alpha olefin.

In yet a further specific embodiment composition (I) further comprises epoxy functional polyorganosiloxane such as epoxy-functional polyorganosiloxane described above.

In one specific embodiment reaction product (a) can comprise two or more cross-linked silicone polymers, specifically two or more three-dimensional cross-linked silicone polymers and most specifically two or more epoxy-functional cross-linked polyorganosiloxanes, wherein the organo groups of epoxy-functional polyorganosiloxane can comprise, in addition to at least one epoxy functional group, the above-described organo groups.

In one specific embodiment herein, "a swelling amount" is an amount that can provide for an increase in volume of reaction product (a) as described herein.

In one embodiment, fluid component, as described above, can be any known or commercially used alkyltrisiloxane provided that alkyltrisiloxane provides for the above stated lower solids content and desirable viscosity in first silicone composition. In one specific embodiment, alkyltrisiloxane (b) is alkyl-substituted trisiloxane. In one embodiment, the term "alkyl" means a saturated straight or branched monovalent hydrocarbon radical. In a specific embodiment, monovalent alkyl groups are selected from linear or branched alkyl groups containing from 1 to 60 carbon atoms per group, such as the non-limiting examples of, methyl, ethyl, propyl, iso-propyl, n-butyl, iso-butyl, sec-butyl, tert-butyl, pentyl, hexyl, heptyl, decyl, and dodecyl. In another specific embodiment there is provided alkyltrisiloxane (b) which is linear alkyltrisiloxane which is high purity material which results from the alkylation of a polyorganosiloxane having the formula (A):

$$MD^H M \quad (A)$$

where $$M = R^A R^B R^C SiO_{1/2}; \text{ and}$$

$$D^H = R^D HSiO_{2/2};$$

where $R^A$, $R^B$, and $R^C$ are independently monovalent hydrocarbon radicals having from one to sixty carbon atoms; and $R^D$ is a monovalent hydrocarbon radical having from one to sixty carbon atoms or hydrogen. In one embodiment, a high purity material as described herein is defined as substantially comprising the alkylated polyorganosiloxane of formula (A). In a specific embodiment herein, alkylation of a polyorganosiloxane having the formula (A) can be accomplished by reacting a polyorganosiloxane having the formula (A) with alkene compound such as ethylene. In a more specific embodiment a high purity material comprises greater than about 90 weight percent of the alkylated polyorganosiloxane of formula (A) based on the total weight of high purity material. In an even more specific embodiment a high purity material comprises greater than about 95 weight percent of the alkylated polyorganosiloxane of formula (A) based on the total weight of the high purity material. In a most specific embodiment a high purity material comprises greater than about 97 weight percent of the alkylated polyorganosiloxane of formula (A) based on the total weight of the high purity material. In one other embodiment herein at least one alkyltrisiloxane (b) can be formed by any known or conventionally used method known to those skilled in the art.

In one specific embodiment, at least one alkyltrisiloxane (b) has the formula:

$$M'D^*{}_r M$$

where $$M \text{ or } M' = R^{24} R^{25} R^{26} SiO_{1/2}; \text{ and,}$$

$$D^* = R^{27} R^{28} SiO_{2/2}$$

where each $R^{24}$, each $R^{25}$, and each $R^{26}$ are independently monovalent hydrocarbon radicals having from one to sixty carbon atoms to allow for M and M' to be different; and where $R^{27}$ and $R^{28}$ are independently monovalent hydrocarbon radicals having from two to sixty carbon atoms; the stoichiometric subscripts r is positive subject to the limitations: that the silicon atom of D* has a pendant group that is other than hydrogen, methyl and polyether, and r is equal to one.

In one specific example some non-limiting examples of alkyltrisiloxane (b) are linear alkyltrisiloxanes selected from the group consisting of ethyltrisiloxane, such as the non-limiting examples of 1,1,1,3,5,5,5-heptamethyl-3-ethyltrisiloxane; octyltrisiloxane, such as the non-limiting example of 1,1,1,3,5,5,5-heptamethyl-3-octyltrisiloxane; hexyltrisiloxane such as the non-limiting example of 1,1,1,3,5,5,5-heptamethyl-3-hexyltrisiloxane, and combinations thereof. In one specific embodiment herein alkyltrisiloxane (b) can be at least one alkyltrisiloxane such as those described in U.S. Patent Application Publication No. 2004/0197284A1 which is incorporated by reference herein in its entirety. In another specific embodiment herein alkyltrisiloxane (b) can be at least one alkyltrisiloxane such as those described in U.S. Patent Application Publication No. 2005/0069564A1 the contents of which are incorporated by reference herein in its entirety. In yet one even more specific embodiment, alkyltrisiloxane (b) can comprise octamethyltrisiloxane (surface tension=17.4 mN/m), sold, for example, under the name DC 200 Fluid 1 cst by the company Dow Corning; 3-pentyl-1,1,1,3,5,5,5-heptamethyltrisiloxane; 1-hexyl-1,1,3,3,5,5,5-heptamethyltrisiloxane; 1,1,1,3,3,5,5-heptamethyl-5-octyltrisiloxane; 1,1,1,3,5,5,5-heptamethyl-3-octyltrisiloxane, sold, for example, under the name "Silsoft 034" by the company General Electric; 1,1,1,3,5,5,5-heptamethyl-3-hexyltrisiloxane (surface tension=20.5 mN/m), sold, for example, under the name "DC 2-1731" by the company Dow Corning; 1,1,3,3,5,5-hexamethyl-1,5-dipropyltrisiloxane; 3-(1-ethylbutyl)-1,1,1,3,5,5,5-heptamethyltrisiloxane; 1,1,1,3,5,5,5-heptamethyl-3-(1-methylpentyl)trisiloxane; 1,5-diethyl-1,1,3,3,5,5-hexamethyltrisiloxane; 1,1,1,3,5,5,5-heptamethyl-3-(1-methylpropyl)trisiloxane; 3-(1,1-dimethylethyl)-1,1,1,3,5,5,5-heptamethyltrisiloxane; 1,1,1,5,5,5-hexamethyl-3,3-bis(1-methylethyl)trisiloxane; 1,1,1,3,3,5,5-hexamethyl-1,5-bis(1-methylpropyl)trisiloxane; 1,5-bis(1,1-dimethylethyl)-1,1,3,3,5,5-hexamethyltrisiloxane; 3-(3,3-dimethylbutyl)-1,1,1,3,5,5,5-heptamethyltrisiloxane; 1,1,1,3,5,5,5-heptamethyl-3-(3-methylbutyl)trisiloxane; 1,1,1,3,5,5,5-heptamethyl-3-(3-methylpentyl)trisiloxane; 1,1,1,3,5,5,5-heptamethyl-3-(2-methylpropyl)trisiloxane; 1-butyl-1,1,3,3,5,5,5-heptamethyltrisiloxane; 1,1,1,3,5,5,5-heptamethyl-3-propyltrisiloxane; 3-isohexyl-1,1,1,3,5,5,5-heptamethyltrisiloxane; 1,3,5-triethyl-1,1,3,5,5-pentamethyltrisiloxane; 3-butyl-1,1,1,3,5,5,5- heptamethyltrisiloxane; 3-tert-pentyl-1,1,1,3,5,5,5-heptamethyltrisiloxane; 1,1,1,5,5,5-hexamethyl-3,3-dipropyltrisiloxane; 3,3-diethyl-1,1,1,5,5,5-hexamethyltrisiloxane; 1,5-dibutyl-1,1,3,3,5,5-hexamethyltrisiloxane; 1,1,1,5,5,5-hexaethyl-3,3-dimethyltrisiloxane; 3,3-dibutyl-1,1,1,5,5,5-hexamethyltrisiloxane; 3-ethyl-1,1,1,3,5,5,5-heptamethyltrisiloxane; 3-heptyl-1,1,1,3,5,5,5-heptamethyltrisiloxane; 1-ethyl-1,1,3,3,5,5,5-heptamethyltrisiloxane; 1,1,1,5,5,5-hexamethyl-3,3-diethyltrisiloxane; 1,1,3,3,5,5-hexamethyl-1,5-diethyltrisiloxane; 1,1,1,3,5,5,5-heptamethyl-3-butyltrisiloxane and combinations thereof. In one specific embodiment reaction product (a) can be homogenized using conventionally known methods specifically using fluid component described herein and more specifically alkyltrisiloxane described herein.

In one specific embodiment alkyltrisiloxane (b) can comprise two or more alkyltrisiloxanes.

In a further specific embodiment herein, first silicone composition can further comprise silicone fluid other than said alkyltrisiloxane. In a more specific embodiment, said silicone fluid other than alkyltrisiloxane can be cyclic siloxane and/or linear silicone fluid such as, decamethylcyclopentasiloxane fluid and/or high molecular weight polyorganosiloxane fluid, respectively. In a most specific embodiment herein said high molecular weight polyorganosiloxane fluid has a greater viscosity relative to alkyltrisiloxane (b) and can be selected from the group consisting of organo polydimethylsiloxanes having a viscosity of specifically from about 1 to about 400, more specifically of from about 3 to about 350, and most specifically from about 5 to about 300 centistokes, wherein the organo groups are any of the above described organo groups. In one specific embodiment organo polydimethylsiloxane can have a viscosity of from about 1 to about 100 centipoise, more specifically 2 to about 50 centipoise and most specifically 5 to about 10 centipoise. In one very specific embodiment, polydimethylsiloxane can have a viscosity of 5 centipoise. In one very specific embodiment, polydimethylsiloxane can have a viscosity of 50 centipoise.

In a specific embodiment, first silicone composition described herein is a solid, typically having a creamy consistency, wherein reaction product (a) act as a means for gelling fluid component to reversibly impart characteristics of a solid to fluid component.

In one specific embodiment herein there is provided silicone gel substantially comprising first silicone composition. In one embodiment herein, the amount of first silicone composition which substantially comprises silicone gel is specifically greater than about 10 weight percent, more specifically greater than about 50 weight percent and most specifically greater than about 90 weight percent based upon the total weight of silicone gel. It will be understood herein that silicone gel as described herein can also have the above-described viscosities and solids content.

In one specific embodiment herein other silicone compositions comprising at least one alkyltrisiloxane (b) can be made by using silicone polymers formed from other cross-linking processes known to those skilled in the art. In one specific embodiment herein there are provided silicone gels substantially comprising other silicone compositions as described above, made by other cross-linking processes known to those skilled in the art, that can also be swollen by at least one alkyltrisiloxane (b) described herein.

In one other embodiment, first silicone composition exhibits high stability and resistance to syneresis, that is, first silicone composition exhibits little or no tendency for fluid to flow from first silicone composition and imparts high stability and syneresis resistance to personal care formulations which include first silicone composition as a component. The high stability and syneresis resistance persists with prolonged aging of such first silicone composition and personal care formulations comprising the same. However, fluid component can be released from reaction product (a) by subjecting first silicone composition to a shearing force, such as, for example, by rubbing first silicone composition between one's fingers, to provide improved sensory feel characteristic of the fluid component of first silicone composition. In one embodiment herein, first silicone composition as described herein, can be utilized as prepared or as the silicone component in emulsions, such as are described in U.S. Pat. Nos. 6,531,540; 6,060,546 and 6,271,295, the contents for all of these patents are incorporated by reference herein in their entirety.

In one embodiment, there is provided a personal care formulation comprising silicone gel substantially comprising first silicone composition as described herein where said personal care formulation is at least one non-limiting example such as those selected from the group consisting of deodorant, antiperspirant, antiperspirant/deodorant, shaving product, skin lotion, moisturizer, toner, bath product, cleansing product, hair care product such as shampoos, conditioners, mousses, styling gels, hair sprays, hair dyes, hair color products, hair bleaches, waving products, hair straighteners, hair frizz control; hair volumizing; manicure product such as nail polish, nail polish remover, nails creams and lotions, cuticle softeners, protective cream such as sunscreen, insect repellent and anti-aging products, color cosmetic such as lipsticks, foundations, face powders, eye liners, eye shadows, blushes, makeup, mascaras, as vehicles for fragrance delivery benefits, and other personal care formulations where silicone components have been conventionally added, as well as drug delivery system for topical application of medicinal composition that is to be applied to the skin.

In a more specific embodiment, the personal care formulation described herein further comprises one or more personal care ingredients. Suitable personal care ingredients include, for example, emollient, moisturizer, humectant, pigment, including pearlescent pigments such as, for example, bismuth oxychloride and titanium dioxide coated mica, colorant, fragrance, biocide, preservative, antioxidant, anti-microbial agent, anti-fungal agent, antiperspirant agent, exfoliant, hormone, enzyme, medicinal compound, vitamin, salt, electrolyte, alcohol, polyol, absorbing agent for ultraviolet radiation, botanical extract, surfactant, silicone oil, organic oil, wax, film former, thickening agent such as, for example, fumed silica or hydrated silica, particulate filler, such as for example, talc, kaolin, starch, modified starch, mica, nylon, clay, such as, for example, bentonite and organo-modified clays, and combinations thereof.

In another embodiment herein first silicone composition can be formed by any known or commercially used process provided that said process provides for the above-described swelling of reaction product (a). In one specific embodiment there is provided a process for producing first silicone composition comprising combining at least one reaction product (a); and, a swelling amount of at least one alkyltrisiloxane (b); to produce first silicone composition possessing substantially the same viscosity, but a lower solids content, than that of second silicone composition described herein.

In one specific embodiment, said process of producing first silicone composition can comprise forming reaction product (a) by a polymerization method selected from the group consisting of addition polymerization, condensation polymerization, cationic polymerization, anionic polymerization, and combinations thereof.

In one embodiment herein, reaction product (a) is prepared in the normal manner through the use of a hydrosilation reaction to attach a vinyl or allyl substituted epoxide onto an Si—H bearing siloxane. SiH containing siloxanes are well known in the art and can be linear, branched, or cyclic in structure. Some non-limiting examples of useful vinyl or allyl substituted epoxides include 4-vinyl cyclohexene oxide, allyl glycidyl ether, limonene oxide, 1,2-epoxy-5-hexene, 1,2-epoxy-7-octene, norbornadiene monoepoxide and 1,2-epoxy-9-decene. In one further embodiment herein, precious metal catalysts suitable for making reaction product (a), alkyltrisiloxane (b) and first silicone composition described herein are well known in the art and include complexes of rhodium, ruthenium, palladium, osmium, iridium and/or platinum. Epoxy-hydride reactions used to form cross-linked silicone network (a) and gels comprising swollen cross-linked silicone network which are made using epoxy-hydride reactions are known to those skilled in the art as is described in U.S. Pat. No. 6,531,540, the contents of which are incorporated herein by reference.

In one specific embodiment, reaction product (a) is a compound which is formed by polymerizing the epoxy functional organosiloxane compound under cationic polymerization conditions and, more specifically, in the presence of fluid component, more specifically a low molecular weight siloxane fluid. In one embodiment, reaction product (a) is can have been polymerized in the presence of fluid component or fluid component mixture to directly form a first silicone composition. In another embodiment, reaction product (a) can have been polymerized in the presence of a first fluid component or first fluid component mixture to form cross-linked polyether siloxane copolymer network which is reaction product (a), and then reaction product (a) so formed, is subsequently swollen with a second fluid component or second fluid component mixture to form first silicone composition described herein; with the second fluid component or second fluid component mixture being the same as or different from first fluid component or first fluid component mixture, provided that said first fluid component(s) and/or second fluid component(s) comprise alkyltrisiloxane (b). In one embodiment herein, the first fluid component(s) can, optionally, be removed from reaction product (a) by, for example, evaporation, prior to addition of second fluid component(s). As a further specific embodiment herein, cross-linked epoxy functional reaction product (a) is polymerized in the absence of fluid component(s) to form reaction product (a), and reaction product (a) is subsequently swollen with fluid component or mixture of fluid components to form first silicone composition described herein, provided that fluid component or mixture of fluid components comprises alkyltrisiloxane (b).

In another embodiment, the polymerization of the epoxy functional organosiloxane is conducted with a sufficient amount of excess hydridosiloxane functionality such that there is residual hydride remaining after polymerization that may be subsequently reacted under conditions suitable for hydrosilylation with one or more alkenyl functional compounds. This is especially advantageous in cases where the alkenyl functional compounds can act as inhibitors of cationic cure. Such alkenyl compounds are those that contain a functionality that can act as an inhibitor of the cationic cure mechanism, e.g. a base. In another embodiment, a small amount of a concentrated hydridosiloxane or hydridosilane compound is added in order to increase the rate of polymerization.

In one specific embodiment herein, there is provided a process of producing first silicone composition comprising where at least one reaction product (a) is produced in the presence of at least one first fluid component and is subsequently swollen, where swelling said reaction product (a) comprises diluting the reaction product (a), that has been produced in the presence of at least one first fluid component, with at least one second fluid component with the proviso that at least one first fluid component and/or at least one second fluid component is alkyltrisiloxane (b).

In one embodiment herein there is provided a silicone gel produced by any process described herein. In another specific embodiment there is provided silicone gel substantially comprising first silicone composition which is produced by the process of producing first silicone composition as described above. In yet a further embodiment herein, there is provided a personal care formulation, such as those described above, comprising silicone gel produced by any process described herein.

In one embodiment herein there is provided silicone gel produced by any process described herein where the silicone gel has a lower solids content and a desirable viscosity as described above.

In one specific embodiment herein there is provided a cosmetic composition comprising silicone gel described herein where silicone gel comprises one or more of the formulations described in Table 4.

In another specific embodiment herein there is provided a sunscreen composition comprising silicone gel described herein where silicone gel comprises the following sunscreen formulation in Table A:

TABLE A

| Ingredient | Wt (%) |
|---|---|
| Part A | |
| Glyceryl Stearate (and) PEG-100 Stearate. (4) | 2.52 |
| Dimethicone 5 cSt (1) | 4.5 |
| Isopropyl Palmitate | 2.7 |
| Example 2, Sample 2 from Table 1 below (1) | 4.5 |
| Caprylyl Methicone (Silsoft 034) (1) | 4.5 |
| PEG-5/PPG-3 Methicone (Silsoft 305) (1) | 1.14 |
| Dimethicone (and) Trimethylsiloxysilicate (SS4267) (1) | 0.90 |
| Tocopherol acetate USP (3) | 0.27 |
| Benzophenone-3 (2) | 2 |
| Octyl MethoxyCinnamate (2) | 3 |
| Butylmethoxydibenzoylmethane (2) | 1.5 |
| TiO2 (C47-60, Sunchemical) | 0.3 |
| Part B | |
| Water deionized | 65.77 |
| Glycerin | 3.60 |
| Niacinamide (3) | 0.90 |
| Panthenol (3) | 0.36 |
| Arbutin (3) | 0.05 |
| Na4EDTA | 0.07 |
| Sodium Ascorbyl phosphate(3) | 0.05 |
| Carbopol 941 | 0.12 |
| Triethanolamine | 0.21 |
| Preservative (2) | 0.06 |
| Fragrance | quantity sufficient |
| Part C | |
| Polyacrylamide (and) C13-C14 Isoparaffin (and) Laureth-7 (5) | 0.90 |

It will be understood that Wt % as used in Table A is weight percent of based on the total weight of the sunscreen formulation.

In one embodiment herein sunscreen composition in Table A is prepared by the following procedure:
1. Combine ingredients of Part A at room temperature, heat to 75 degrees celsius
2. Combine ingredients of Part B, heat to 75 degrees celsius.
3. Slowly add B to A, carefully monitoring the temperature.
4. Add C.
5. Cool to 30 degrees celsius with moderate mixing. Add fragrance and preservative.
6. Homogenize It will be understood that the ingredients of the sunscreen composition in Table A are available under the trade name or from the supplier indicated by the number in parentheses next to each ingredient in Table A which is defined in the list below:

Trade Names/Suppliers
   (1) GE Advanced Materials, Silicones
   (2) ISP
   (3) BASF
   (4) Uniqema
   (5) Seppic It will also be understood that quantity sufficient as used in Table A can be adjusted by the end user to specific desired amounts.

The examples below are given for the purpose of illustrating the invention of the instant case. They are not being given for any purpose of setting limitations on the embodiments described herein. All weights are weight percent based on the total weight of first silicone composition unless stated otherwise.

EXAMPLES

The use of alkyltrisiloxanes as fluid component for first silicone composition(s) provides a means of obtaining high viscosity silicone gel at low solids concentrations. This result is unexpected when compared with other linear silicone fluids, which are typically much less effective silicone fluid components than corresponding cyclic silicone fluids and therefore require increasing amounts of cross-linked silicone network such as reaction product (a) to provide first silicone composition with desired properties. The addition of alkyltrisiloxane as fluid component also offers a number of formulation and sensory benefits when compared with silicone compositions swelled by other linear polydimethylsiloxane fluids. A number of silicone gels have been prepared using both octyltrisiloxane (OTS) and ethyltrisiloxane (ETS) as the fluid component either alone or in combination with other silicone fluids. It is quite clear from these studies that OTS and ETS fluids function as more efficient gel fluid components than other linear polydimethylsiloxane fluids. Also, when these gels with trisiloxanes are formulated into personal care formulations, the personal care formulations show a number of functional or aesthetic performance benefits not seen with gels swelled by other fluid component(s); some non-limiting examples of such sensory benefits include decreased balling on the skin, general feel of the personal care formulation on the skin and improved thickening of personal care formulations.

Comparative Example 260 grams (g) of a silicone hydride fluid with the approximate composition $M^H D_{133} D^H_{2.5} M^H$ was mixed with 8.5 g of vinyl cyclohexene oxide, 21.7 g of Alpha Olefin (Gulftene C30+ from Chevron), 630 g of decamethyl cylcopentasiloxane ($D_5$) and 0.075 g of platinum catalyst solution, Karstedt's Catalyst. The mixture was heated to 90 degrees celsius and then mixed for 45 minutes. Then 9.7 g of another silicone hydride fluid, $MD^H_{50}M$ in 80 g of $D_5$ was added to the hot reaction mixture. This was stirred at 90 degrees celsius for another 4 hours and then the reaction was quenched with the addition of a terminal olefin which was $C_{16-18}$ alpha olefin from Innovene. The resulting material had a solids content of 29.8 weight percent and extractables of 20 weight percent based upon the total weight of reaction product (a). Then 250 g of this material was diluted with 350 g of $D_5$, and then passed through a Gaulin homogenizer one time at 9000 pounds per square inch (psi). The resulting gel (Sample 1) had a solids content of about 12.5 weight percent based upon the total weight of first silicone gel and a viscosity of 183,000 centipoise (cP) at 24 hours.

Example 1

260 g of a silicone hydride fluid with the approximate composition $M^H D_{133} D^H_{2.5} M^H$ was mixed with 8.5 g of vinyl cyclohexene oxide, 21.7 g of alpha Olefin (Gulftene C30+ from Chevron), 630 g of ethyltrisiloxane and 0.075 g of platinum catalyst solution (Karstead's catalyst). The mixture was heated to 90 degrees celsius and then mixed for 45 minutes. Then 9.7 g of another silicone hydride, $MD^H_{50}M$ in 80 g of ethyltrisiloxane was added to the hot reaction mixture. This was stirred at 90 degrees celsius for another 4 hours and then the reaction was quenched with the addition of a terminal olefin which was $C_{16-18}$ alphaolefin from Innovene. The resulting material had a solids content of 29.8 weight percent and extractables of 24.5 weight percent based upon the total weight of reaction product (a). Then 250 g of this material was diluted with 350 g of ethyltrisiloxane and passed through a Gaulin homogenizer one time at 9000 psi. The resulting material (Sample 2) had a solids content of about 12.5 weight percent based upon the total weight of the silicone gel and a viscosity of 220,000 cP at 24 hours. When 250 g of this 29.8 weight percent cross-linked silicone powder was homogenized one time with 350 g of octyltrisiloxane, the resulting gel (Sample 2-a) had a solids content of about 12.5 weight percent based upon the total weight of silicone gel and a viscosity of 205,000 cP at 24 hours.

Example 2

260 g of a silicone hydride fluid with the approximate composition $M^H D_{133} D^H_{2.5} M^H$ was mixed with 8.5 g of vinyl cyclohexene oxide, 7.4 g of $C_{16-18}$ alpha olefin from Innovene, 630 g of ethyltrisiloxane and 0.075 g of platinum catalyst solution (Karstedt's Catalyst). The mixture was heated to 90 degrees celsius and then mixed for 45 minutes. Then 9.7 g of another silicone hydride, $MD^H_{50}M$ in 80 g of ethyltrisiloxane was added to the hot reaction mixture. This was stirred at 90 degrees celsius for another 4 hours and then the reaction was quenched with the addition of a terminal olefin ($C_{16-18}$ from Innovene) The resulting material had a solids content of 31 weight percent and extractables of 18 weight percent based upon the total weight of reaction product (a). Then 250 g of this material was diluted with 350 g of ethyltrisiloxane and passed through a Gaulin homogenizer one time at 9000 psi. The resulting material (Sample 3) had a solids content of about 12.5 weight percent based upon the total weight of silicone gel and a viscosity of 254,000 cP at 24 hours. When 250 g of this 31 weight percent cross-linked silicone powder, was homogenized with 350 g of octyltrisiloxane, the resulting gel (Sample 3-a) had a solids content of about 12.5 weight percent based upon the total weight of silicone gel and a viscosity of 185,000 cP at 24 hours.

TABLE 1

Summary of Results of Examples 1 and 2

| | Sample | Alkyl Chain Length in Number of Carbon Atoms | Fluid Component | Extractables (weight-percent of reaction product (a)) | Gel Solids (weight-percent of silicone gel) | Viscosity (cP) |
|---|---|---|---|---|---|---|
| Comparative Example | 1 | 30-45 | D5 | 20 | 12.5 | 183,000 |
| Example 1 | 2 | 30-45 | ETS | 24.5 | 12.5 | 220,000 |
| | 2a | 30-45 | ETS/OTS | 24.5 | 12.5 | 205,000 |
| Example 2 | 3 | 16-18 | ETS | 18 | 12.5 | 254,000 |
| | 3a | 16-18 | ETS/OTS | 18 | 12.5 | 185,000 |

As the summary of results in Table 1 indicates, the decamethyl cylcopentasiloxane (D5) and ethyltrisiloxane have similar gel-swelling efficiencies when cross-linked polymer alkyl chain length and extractables measures are considered. Typically, higher extractables measures results in somewhat higher viscosity materials. Also noted from these experiments is that octyltrisiloxane is a less efficient swelling agent than ethyltrisiloxane as shown in Sample-2a and Sample-3a.

Example 3

Preparation of the reaction product (a), and its swelling by a range of organosiloxane fluids. 260 g of a silicone hydride fluid with the approximate composition $M^H D_{133} D^H{}_{2.5} M^H$ was mixed with 8.5 g of vinyl cyclohexene oxide, 15.4 g of $C_{16-18}$ alpha olefin from Innovene, 630 g of polydimethylsiloxane (5 cP) and 0.075 g of platinum catalyst solution (Karstedt's Catalyst). The mixture was heated to 90° C. and then mixed for 45 minutes. Then 8.6 g of another silicone hydride, $MD^H{}_{50}M$, in 80 g of polydimethylsiloxane (5 cP) was added to the hot reaction mixture. This was stirred at 90° C. for another 4 hours and then the reaction was quenched with the addition of a terminal olefin ($C_{16-18}$ alpha olefin from Innovene). The resulting material had a solids content of 30%, based on the total weight of reaction product (a). The following swollen silicone gels were prepared by passing blends of reaction product (a) powder with mixtures of octyltrisiloxane and 5 cP polydimethylsiloxane (PDMS) through the Gaulin homogenizer at 9,000 psi twice. The solids and viscosities of the resulting silicone gels (Samples 4-14) are listed in the following table; (Table 2).

TABLE 2

Silicone gels with linear silicones as swelling agents

| Sample | Amount in grams of reaction product (a) | Amount in grams of octyltrisiloxane | Amount in grams of 5 cP PDMS | Solids in gel (weight-percent of silicone gel) | Viscosity at 1 week (cP) |
|---|---|---|---|---|---|
| 4 | 19,340 | 0 | 16,980 | 16 | 90,000 |
| 5 | 533 | 233 | 233 | 16 | 114,000 |
| 6 | 533 | 467 | 0 | 16 | 134,000 |
| 7 | 20,566 | 0 | 15,754 | 17 | 110,000 |
| 8 | 566 | 217 | 217 | 17 | 143,000 |
| 9 | 566 | 324 | 108 | 17 | 173,500 |
| 10 | 566 | 434 | 0 | 17 | 204,500 |
| 11 | 21,792 | 0 | 14,528 | 18 | 180,000 |
| 12 | 600 | 200 | 200 | 18 | 219,500 |
| 13 | 600 | 400 | 0 | 18 | 277,50b0 |
| 14 | 633 | 364 | 0 | 19 | 329,500 |

As the results in this example clearly illustrate, increasing the proportion of octyltrisiloxane to 5 cP PDMS increases the viscosity of the silicone gel at a given level of reaction product (a) solids in the silicone gel. Therefore alkyltrisiloxane is a more efficient fluid component for silicone gel than the linear 5 cP PDMS fluid.

Also, the alkyltrisiloxane is able to effectively swell reaction product (a) in the presence of a linear higher molecular weight PDMS fluid. Therefore, combination of PDMS and alkyltrisiloxane in silicone gel provides unique end user benefits, said combination of PDMS and alkyltrisiloxane will also be a more efficient swelling fluid component for reaction product (a) than PDMS used alone.

Example 4

260 grams (g) of a silicone hydride fluid with the approximate composition $M^H D_{133} D^H{}_{2.5} M^H$ was mixed with 8.5 g of vinyl cyclohexene oxide, 21.7 g of Alpha Olefin (Gulftene C30+ from Chevron), 630 g of decamethyl cylcopentasiloxane ($D_5$) and 0.075 g of platinum catalyst solution, Karstedt's Catalyst. The mixture was heated to 90 degrees celsius and then mixed for 45 minutes. Then 9.7 g of another silicone hydride fluid, $MD^H{}_{50}M$ in 80 g of $D_5$ was added to the hot reaction mixture. This was stirred at 90 degrees celsius for another 4 hours and then the reaction was quenched with the addition of a terminal olefin which was $C_{16-18}$ alpha olefin from Innovene. The resulting material had a solids content of 30%, and extractables of 15 weight percent based on the total weight of reaction product (a). The following silicone gels (Samples 15-20) were prepared by passing blends of reaction product (a) powder with mixtures of octyltrisiloxane and decamethyl cyclopentasiloxane through the Gaulin homogenizer at 9,000 psi. The solids and viscosities of the resulting gels are listed in the following table (Table 3).

TABLE 3

Silicone Gels with trisiloxanes as fluid components

| Sample | Amount in grams of reaction product (a) | Amount in grams of octyltri-siloxane | Amount in grams of D5 | Solids in gel (weight-percent of silicone gel) | Viscosity at 1 wk (cP) |
|---|---|---|---|---|---|
| 15 | 247 | 0 | 353 | 12.5 | 126,000 |
| 16 | 247 | 176 | 176 | 12.5 | 108,000 |
| 17 | 247 | 353 | 0 | 12.5 | 83,500 |
| 18 | 297 | 0 | 303 | 15 | 334,500 |
| 19 | 297 | 152 | 152 | 15 | 204,000 |
| 20 | 297 | 303 | 0 | 15 | 200,500 |

As the results in Table 3 indicate, blending octyltrisiloxane with decamethyl cyclopentasiloxane provides silicone gels with lower viscosity implying that $D_5$ is a more effective fluid component than octyltrisiloxane.

Upon analysis of Examples 1-5, the following trend is very easy to ascertain: decamethyl cyclopentasiloxane (D5)≅ethyltrisiloxane>octyltrisiloxane>5 cP PDMS fluid>higher molecular weight PDMS fluids in ranking of ability to swell reaction product (a).

Example 5

Enhanced Thickening Performance of Silicone Gel in Cosmetic Formulations: When silicone gels are formulated into "cream to powder" foundations, gels containing alkyltrisiloxanes provide much higher viscosity products than gel containing D5 alone (Sample 1); that are easy to spread with very pleasant sensory properties and which exhibit enhanced product stability. The formulations (1-4) are shown in the table below (Table 4). It will be understood that weight percent as used in Table 4 for the formulations 1-4 is weight percent based on the total weight of the formulation.

TABLE 4

Foundation Formulations

| Ingredient | Formulation 1 weight percent | Formulation 2 weight percent | Formulation 3 weight percent | Formulation 4 weight percent |
|---|---|---|---|---|
| Part A | | | | |
| Sample 1 (Example 1) (D5) | 44.5 | | | |
| Sample 2 (Example 2) (ETS) | | 44.5 | | |
| Sample 16 (Example 5) (D5/OTS) | | | 44.5 | |
| Sample 19 (Example 5) (D5/OTS) | | | | 44.5 |
| Cyclopentasiloxane | 30.2 | 30.2 | 30.2 | 30.2 |
| Phenylpropyldimethylsiloxysilicate | 3.0 | 3.0 | 3.0 | 3.0 |
| Cyclopentasiloxane & Dimethicone | 6.6 | 6.6 | 6.6 | 6.6 |
| Part B | | | | |
| Polymethylsilsequioxane | 11.8 | 11.8 | 11.8 | 11.8 |
| Part C | | | | |
| TiO$_2$ | 2.8 | 2.8 | 2.8 | 2.8 |
| Colored Pigments | 1.1 | 1.1 | 1.1 | 1.1 |
| Viscosity of final Foundations | 9,500 cP | 28,000 cP | 62,000 cP | 100,000 cP |

These formulations are made by mixing all of the parts A, B and C for 5 to 10 minutes with an overhead stirrer at 3000 rotations per minute (rpm). As noted by the viscosity measurements of the final products, the use of ethyltrisiloxane or octyltrisiloxane in the silicone gels provides much higher viscosity cream to powder foundations (Formulations 2-4) than silicone gels without the trisiloxane (Formulation 1). These foundation formulations are also easy to spread with a differentiating sensory property that provides a powdery after feel for the product.

While the above description comprises many specifics, these specifics should not be construed as limitations, but merely as exemplifications of specific embodiments thereof. Those skilled in the art will envision many other embodiments within the scope and spirit of the description as defined by the claims appended hereto.

The invention claimed is:

1. A first silicone composition comprising:
   a) the reaction product of $$M_a M^H_b M^{vi}_c M^E_d D_e D^H_f D^{vi}_g D^E_h T_i T^H_j T^{vi}_k T^E_L Q_m$$

where $M = R^1R^2R^3SiO_{1/2}$;

$M^H = R^4R^5HSiO_{1/2}$;

$M^{vi} = R^6R^7R^8SiO_{1/2}$;

$M^E = R^9R^{10}R^ESiO_{1/2}$;

$D = R^{11}R^{12}SiO_{2/2}$;

$D^H = R^{13}HSiO_{2/2}$;

$D^{VI} = R^{14}R^{15}SiO_{2/2}$;

$D^E = R^{16}R^ESiO_{2/2}$ $T = R^{17}SiO_{3/2}$ $T^H = HSiO_{3/2}$;

$T^{vi} = R^{18}SiO_{3/2}$;

$T^E = R^ESiO_{3/2}$; and $Q = SiO_{4/2}$ where $R^1$, $R^2$, $R^3$, $R^{11}$, $R^{12}$ and $R^{17}$ are independently monovalent hydrocarbon radicals having from one to sixty carbon atoms; $R^4$, $R^5$ and $R^{13}$ are independently monovalent hydrocarbon radicals having from one to sixty carbon atoms or hydrogen; $R^6$ is a monovalent unsaturated hydrocarbon radical having from two to ten carbon atoms, and $R^7$ and $R^8$ are independently monovalent hydrocarbon radicals having from one to sixty carbon atoms; $R^{14}$ is a monovalent unsaturated hydrocarbon radical having from two to ten carbon atoms; and $R^{15}$ is a monovalent hydrocarbon radical having from one to sixty carbon atoms; $R^{18}$ is a monovalent unsaturated hydrocarbon radical having from two to ten carbon atoms; $R^9$, $R^{10}$ and $R^{16}$ are independently monovalent hydrocarbon radicals having from one to sixty carbon atoms or $R^E$; each $R^E$ is independently a monovalent hydrocarbon radical containing one or more oxirane moieties having from one to sixty carbon atoms; the stoichiometric subscripts a, b, c, d, e, f, g, h, i, j, k, L, and m, are either zero or positive subject to the following limitations: a+b+c+d>1; d+h+L≧1 and b+f+j≧1; and, b) a swelling amount of linear alkyltrisiloxane wherein said reaction product is swollen by said linear alkyltrisiloxane to form a first silicone composition and wherein said first silicone composition possesses a lower solids content than a solids content present in a second silicone composition comprising said reaction product and a linear silicone fluid other than linear alkyltrisiloxane, whereby second silicone composition and first silicone composition have equivalent viscosities.

2. The first silicone composition of claim 1, where first silicone composition has a given cross-linked structure and a given cross-link density and said lower solids content of first silicone composition is at least about 10 percent lower than the solids content for second silicone composition which has an equivalent cross-linked structure and an equivalent cross-link density to first silicone composition; and where first silicone composition has a viscosity of greater than about 100,000 centistokes.

3. The first silicone composition of claim 1, where first silicone composition has a given cross-linked structure and a given cross-link density and said lower solids content of first silicone composition is at least about 25 percent lower than the solids content for second silicone composition which has an equivalent cross-linked structure and an equivalent cross-link density to first silicone composition; and where first silicone composition has a viscosity of greater than about 150,000 centistokes.

4. The first silicone composition of claim 1, where first silicone composition has a given cross-linked structure and a given cross-link density and said lower solids content of first silicone composition is at least about 40 percent lower than the solids content for second silicone composition which has an equivalent cross-linked structure and an equivalent cross-link density to first silicone composition; and where first silicone composition has a viscosity of greater than about 200,000 centistokes.

5. The first silicone composition of claim 1 where reaction product (a) comprises the reaction product of (I) a composition comprising the formula:

$$M^H_n D_o D^H_p M^H_{2-n}$$

where $$M^H = R^{19}R^{20}HSiO_{1/2};$$

$$D = R^{21}R^{22}SiO_{2/2}; \text{ and,}$$

$$D^H = R^{23}HSiO_{2/2}$$

where $R^{19}$, $R^{20}$, and $R^{23}$ are independently monovalent hydrocarbon radicals having from one to sixty carbon atoms or hydrogen; $R^{21}$ and $R^{22}$ are independently monovalent hydrocarbon radicals having from one to sixty carbon atoms; the stoichiometric subscripts n, o, and p are zero or positive subject to the limitations: o is a number greater than 10, p is a number from zero to about 20, n is a number from zero to two, subject to the limitation that n+p is from 1 to about 20; (II) alkenyl cycloalkylene oxide; (III) alpha-olefin fraction; (IV) linear alkyltrisiloxane and optionally cyclic siloxane, (V) platinum catalyst; (VI) epoxide polymerization catalyst formed through the interaction of platinum with a Si—H bond containing compound in fluid component; and (VII) agent for quenching residual functionality.

6. The first silicone composition of claim 1 where at least one linear alkyltrisiloxane (b) material results from the alkylation of a polyorganosiloxane having the formula (A):

$$MD^HM \quad (A)$$

where $$M = R^A R^B R^C SiO_{1/2}; \text{ and}$$

$$D^H = R^D HSiO_{2/2};$$

where $R^A$, $R^B$, and $R^C$ are independently monovalent hydrocarbon radicals having from one to sixty carbon atoms; and $R^D$ is a monovalent hydrocarbon radical having from one to sixty carbon atoms or hydrogen.

7. The first silicone composition of claim 1 where at least one linear alkyltrisiloxane (b) has the formula:

$$M'D^*_r M$$

where $$M \text{ or } M' = R^{24}R^{25}R^{26}SiO_{1/2}; \text{ and,}$$

$$D^* = R^{27}R^{28}SiO_{2/2}$$

where each $R^{24}$, each $R^{25}$, and each $R^{26}$ are independently monovalent hydrocarbon radicals having from one to sixty carbon atoms to allow for M and M' to be different; and where $R^{27}$ and $R^{28}$ are each independently monovalent hydrocarbon radicals having from one to sixty carbon atoms, provided that at least one of $R^{27}$ and $R^{28}$ is a monovalent hydrocarbon radical having from two to sixty carbon atoms; and r is equal to one.

8. The first silicone composition of claim 1 where at least one linear alkyltrisiloxane is selected from the group consisting of ethyltrisiloxane, octyltrisiloxane, hexyltrisiloxane, and combinations thereof.

9. The first silicone composition of claim 1 where at least one linear alkyltrisiloxane is selected from the group consisting of 1,1,1,3,5,5,5-heptamethyl-3-ethyltrisiloxane; 1,1,1,3,5,5,5-heptamethyl-3-octyltrisiloxane; 1,1,1,3,5,5,5-heptamethyl-3-hexyltrisiloxane, octamethyltrisiloxane; 3-pentyl-1,1,1,3,5,5,5-heptamethyltrisiloxane; 1-hexyl-1,1,3,3,5,5,5-heptamethyltrisiloxane; 1,1,1,3,3,5,5-heptamethyl-5-octyltrisiloxane; 1,1,1,3,5,5,5-heptamethyl-3-octyltrisiloxane; 1,1,1,3,5,5,5-heptamethyl-3-hexyltrisiloxane; 1,1,3,3,5,5-hexamethyl-1,5-dipropyltrisiloxane; 3-(1-ethylbutyl)-1,1,1,3,5,5,5-heptarnethyltrisiloxane; 1,1,1,3,5,5,5-heptamethyl-3-(1-methylpentyl)trisiloxane; 1,5-diethyl-1,1,3,3,5,5-hexamethyltrisiloxane; 1,1,1,3,5,5,5-heptamethyl-3-(1-methylpropyl)trisiloxane; 3-(1,1-dimethylethyl)-1,1,1,3,5,5,5-heptamethyltrisiloxane; 1,1,1,3,5,5-hexamethyl-3,3-bis(1-methylethyl)trisiloxane; 1,1,1,3,3,5,5-hexamethyl-1,5-bis(1-methylpropyl)trisiloxane; 1,5-bis(1,1-dimethylethyl)-1,1,3,3,5,5-hexamethyltrisiloxane; 3-(3,3-dimethylbutyl)-1,1,1,3,5,5,5-heptamethyltrisiloxane; 1,1,1,3,5,5,5-heptamethyl-3-(3-methylbutyl)trisiloxane; 1,1,1,3,5,5,5-heptamethyl-3-(3-methylpentyl)trisiloxane; 1,1,1,3,5,5,5-heptamethyl-3-(2-methylpropyl)trisiloxane; 1-butyl-1,1,3,3,5,5,5-heptamethyltrisiloxane; 1,1,1,3,5,5,5-heptamethyl-3-propyltrisiloxane; 3-isohexyl-1,1,1,3,5,5,5-heptamethyltrisiloxane; 1,3,5-triethyl-1,1,3,5,5-pentamethyltrisiloxane; 3-butyl-1,1,1,3,5,5,5-heptamethyltrisiloxane; 3-tert-pentyl-1,1,1,3,5,5,5-heptamethyltrisiloxane; 1,1,1,5,5,5-hexamethyl-3,3-dipropyltrisiloxane; 3,3-diethyl-1,1,1,5,5,5-hexamethyltrisiloxane; 1,5-dibutyl-1,1,3,3,5,5-hexamethyltrisiloxane; 1,1,1,5,5,5-hexaethyl-3,3-dimethyltrisiloxane; 3,3-dibutyl-1,1,1,5,5,5-hexamethyltrisiloxane; 3-ethyl-1,1,1,3,5,5,5-heptamethyltrisiloxane; 3-heptyl-1,1,1,3,5,5,5-heptamethyltrisiloxane; 1-ethyl-1,1,3,3,5,5,5-heptamethyltrisiloxane; 1,1,1,5,5,5-hexamethyl-3,3-diethyltrisiloxane; 1,1,3,3,5,5-hexamethyl-1,5- diethyltrisiloxane; 1,1,1,3,5,5,5-heptamethyl-3-butyltrisiloxane and combinations thereof.

10. A silicone gel substantially comprising first silicone composition of claim 1.

11. A silicone gel substantially comprising first silicone composition of claim 2.

12. A silicone gel substantially comprising first silicone composition of claim 3.

13. A silicone gel substantially comprising first silicone composition of claim 4.

14. A silicone gel substantially comprising first silicone composition of claim 7.

15. A personal care formulation comprising the silicone gel of claim 10 where the personal care formulation is selected from the group consisting of deodorant, antiperspirant, antiperspirant/deodorant, shaving product, skin lotion, moisturizer, toner, bath product, cleansing product, hair care product manicure product, protective cream, color cosmetic, a vehicle for fragrance delivery benefits, drug delivery system for topical application of medicinal composition that is to be applied to the skin, and combinations thereof.

16. The personal care formulation of claim 15 further comprising personal care ingredient selected from the group consisting of emollient, moisturizer, humectant, pigment, coated mica, colorant, fragrance, biocide, preservative, antioxidant, anti-microbial agent, anti-fungal agent, antiperspirant agent, exfoliant, hormone, enzyme, medicinal compound, vitamin, salt, electrolyte, alcohol, polyol, absorbing agent for ultraviolet radiation, botanical extract, surfactant, silicone oil, organic oil, wax, film former, thickening agent, particulate filler, clay, and combinations thereof.

17. A process for producing a first silicone composition comprising:
combining:
  a) the reaction product of $$M_a M^H_b H^{vi}_c M^E_d D_e D^H_f D^{vi}_g D^E_h T_i T^H_j T^{vi}_k T^E_L Q_m$$

where $$M = R^1 R^2 R^3 SiO_{1/2};$$

$$M^H = R^4 R^5 HSiO_{1/2};$$

$$M^{vi} = R^6 R^7 R^8 SiO_{1/2};$$

$$M^E = R^9 R^{10} R^E SiO_{1/2};$$

$$D = R^{11} R^{12} SiO_{2/2};$$

$$D^H = R^{11} HSiO_{2/2};$$

$$D^{vi} = R^{14} R^{15} SiO_{2/2};$$

$$D^E = R^{16} R^E SiO_{2/2}$$

$$T = R^{17} SiO_{3/2}$$

$$T^H = HSiO_{3/2};$$

$$T^{vi} = R^{18} SiO_{3/2};$$

$$T^E = R^E SiO_{3/2}; \text{ and}$$

$$Q = SiO_{4/2};$$

where $R^1$, $R^2$, $R^3$, $R^{11}$, $R^{12}$ and $R^{17}$ are independently monovalent hydrocarbon radicals having from one to sixty carbon atoms; $R^4$, $R^5$ and $R^{13}$ are independently monovalent hydrocarbon radicals having from one to sixty carbon atoms or hydrogen; $R^6$ is a monovalent unsaturated hydrocarbon radical having from two to ten carbon atoms, and $R^7$ and $R^8$ are independently monovalent hydrocarbon radicals having from one to sixty carbon atoms; $R^{14}$ is a monovalent unsaturated hydrocarbon radical having from two to ten carbon atoms; and $R^{15}$ is a monovalent hydrocarbon radical having from one to sixty carbon atoms; $R^{18}$ is a monovalent unsaturated hydrocarbon radical having from two to ten carbon atoms; $R^9$, $R^{10}$ and $R^{i6}$ are independently monovalent hydrocarbon radicals having from one to sixty carbon atoms or $R^E$; each $R^E$ is independently a monovalent hydrocarbon radical containing one or more oxirane moieties having from one to sixty carbon atoms; the stoichiometric subscripts a, b, c, d, e, f, g, h, i, j, k, L, and m, are either zero or positive subject to the following limitations: $a+b+c+d>1$; $d+h+L \geq 1$ and $b+f+j \geq 1$; and, b) a swelling amount of linear alkyltrisiloxane wherein said reaction product is swollen by said linear alkyltrisiloxane to form a first silicone composition and wherein said first silicone composition possesses a lower solids content than a solids content present in a second silicone composition comprising said reaction product and a linear silicone fluid other than linear alkyltrisiloxane, whereby second silicone composition and first silicone composition have equivalent viscosities.

18. The process of claim 17 where first silicone composition has a given cross-linked structure and a given cross-link density and said lower solids content of first silicone composition is at least about 10 percent lower than the solids content for second silicone composition which has an equivalent cross-linked structure and an equivalent cross-link density to first silicone composition; and where first silicone composition has a viscosity of greater than about 100,000 centistokes.

19. The process of claim 17 where first silicone composition has a given cross-linked structure and a given cross-link density and said lower solids content of first silicone composition is at least about 25 percent lower than the solids content for second silicone composition which has an equivalent cross-linked structure and an equivalent cross-link density to first silicone composition; and where first silicone composition has a viscosity of greater than about 150,000 centistokes.

20. The process of claim 17 where first silicone composition has a given cross-linked structure and a given cross-link density and said lower solids content of first silicone composition is at least about 40 percent lower than the solids content for second silicone composition which has an equivalent cross-linked structure and an equivalent cross-link density to first silicone composition; and where first silicone composition has a viscosity of greater than about 200,000 centistokes.

21. The process of claim 17 where at least one linear alkyltrisiloxane (b) has the formula $$M'D^*_r M$$

where $$M \text{ or } M' = R^{24} R^{25} R^{26} SiO_{1/2}; \text{ and,}$$

$$D^* = R^{27} R^{28} SiO_{2/2}$$

where each $R^{24}$, each $R^{25}$, and each $R^{26}$ are independently monovalent hydrocarbon radicals having from one to sixty carbon atoms to allow for M and M' to be different; and where $R^{27}$ and $R^{28}$ are each independently monovalent hydrocarbon radicals having from one to sixty carbon atoms, provided that at least one of $R^{27}$ and $R^{28}$ is a monovalent hydrocarbon radical having from two to sixty carbon atoms; and r is equal to one.

22. The process of claim 17 further comprising where reaction product (a) is produced in the presence of at least one first fluid component and is subsequently swollen, where swelling said reaction product (a) comprises diluting the reaction product (a), that has been produced in the presence of at least one first fluid component, with at least one second fluid component with the proviso that at least one first fluid component and/or at least one second fluid component is linear alkyltrisiloxane (b).

23. A silicone gel substantially comprising the first silicone composition made by the process of claim 17.

24. A silicone gel substantially comprising the first silicone composition made by the process of claim 21.

25. A silicone gel substantially comprising the first silicone composition made by the process of claim 22.

26. A personal care formulation comprising the first silicone composition produced by the process of claim 17 where the personal care formulation is selected from the group consisting of deodorant, antiperspirant, antiperspirant/deodorant, shaving product, skin lotion, moisturizer, toner, bath product, cleansing product, hair care product manicure product, protective cream, color cosmetic, a vehicle for fragrance delivery benefits, drug delivery system for topical application of medicinal composition that is to be applied to the skin, and combinations thereof.

27. The personal care formulation of claim 26 further comprising personal care ingredient selected from the group consisting of emollient, moisturizer, humectant, pigment, coated mica, colorant, fragrance, biocide, preservative, antioxidant, anti-microbial agent, anti-fungal agent, antiperspirant agent, exfoliant, hormone, enzyme, medicinal compound, vitamin, salt, electrolyte, alcohol, polyol, absorbing agent for ultraviolet radiation, botanical extract, surfactant, silicone oil, organic oil, wax, film former, thickening agent, particulate filler, clay, and combinations thereof.

28. A personal care formulation comprising the first silicone composition produced by the process of claim 22 where the personal care formulation is selected from the group consisting of deodorants, antiperspirants, antiperspirant/deodorants, shaving products, skin lotions, moisturizers, toners, bath products, cleansing products, hair care products, manicure products, protective creams, color cosmetics, a vehicle for fragrance delivery benefits, drug delivery systems for topical application of medical compositions that are to be applied to the skin, and combinations thereof.

29. The personal care formulation of claim 28 further comprising personal care ingredient selected from the group consisting of emollient, moisturizer, humectant, pigment, coated mica, colorant, fragrance, biocide, preservative, antioxidant, anti-microbial agent, anti-fungal agent, antiperspirant agent, exfoliant, hormone, enzyme, medicinal compound, vitamin, salt, electrolyte, alcohol, polyol, absorbing agent for ultraviolet radiation, botanical extract, surfactant, silicone oil, organic oil, wax, film former, thickening agent, particulate filler, clay, and combinations thereof.

* * * * *